United States Patent [19]

Leung

[11] Patent Number: 5,459,153

[45] Date of Patent: Oct. 17, 1995

[54] COMPOSITION AND METHODS FOR TREATMENT OF ACNE VULGARIS AND FOR RETARDATION OF AGING

[76] Inventor: Lit-Hung Leung, Room 502, Dragon Seed Building., 39 Queen's Road Central, Hong Kong, Hong Kong

[21] Appl. No.: 580,019

[22] Filed: Sep. 10, 1990

[30] Foreign Application Priority Data

Mar. 27, 1990 [GB] United Kingdom .................... 9006785

[51] Int. Cl.$^6$ ..................... A61K 31/44; A61K 31/415; A61K 31/195
[52] U.S. Cl. .......................... 514/356; 514/392; 514/563; 514/859
[58] Field of Search ....................... 514/356, 387, 514/561, 859, 563, 392

[56] References Cited

U.S. PATENT DOCUMENTS 3,729,568  4/1973  Kligman .................. 424/318
4,505,896  3/1985  Bernstein ................. 424/164
4,857,321  8/1989  Thomas .................... 424/95
4,885,157  12/1989  Fiaschetti ................ 424/59

OTHER PUBLICATIONS

Handbook of Nonprescription Drugs, 5th ed, 1977, pp. 148–161.
Chemical Abstracts 112:164983e (Morrison), 1990.
Chemical Abstracts 112:84170x (Kawaviri et al), 1990.

Primary Examiner—Raymond Henley, III
Attorney, Agent, or Firm—Thompson, Hine and Flory

[57] ABSTRACT

A method and pharmaceutical composition are described for treatment of acne vulgaris which comprises administering to a patient suffering from acne vulgaris an effective amount of a pharmaceutical composition comprising pantothenic acid or a derivative thereof which generates pantothenic acid in the body to form Coenzyme A (CoA), nicotinic acid or a derivative thereof which generates nicotinamide adenine dinucleotide (NAD) or nicotinamide adenine dinucleotide phosphate (NADP) in the body, and biotin, or a mixture thereof.

22 Claims, No Drawings

COMPOSITION AND METHODS FOR TREATMENT OF ACNE VULGARIS AND FOR RETARDATION OF AGING

FIELD OF THE INVENTION

This invention relates to methods using pantothenic acid, supplemented with nicotinic acid and biotin for treating the condition acne vulgaris. In addition, through direct influence on the structural effect on the cell and cell membrane, and indirectly through the participation of pantothenic acid in the synthesis of the estrogens, the composition favorably affects the skin in a healthy manner, and is believed ultimately to retard the effect of aging of the skin, and generally improve the quality of the skin, particularly the human facial skin.

BACKGROUND OF THE INVENTION

Acne vulgaris is perhaps the commonest disease of the skin. It is estimated that 85–90% of the population aged between 10–25 are affected. It is a disorder of the pilosebaceous unit, which consists of a sebaceous gland draining into a hair follicle via a sebaceous duct. These glands are particularly large and active on the forehead, nose, face, neck, and the front and back of the upper chest, and they are lined on the outside by a layer of basement membrane. What appears to happen when an acne is formed is that the cells at the periphery of the gland, that is, the cells just above the basement membrane, start to be filled with fat droplets. As these cells also serve the function of generating new cells, so, when new cells are generated, the original cells that are beginning to be filled with fat droplets are being displaced towards the center of the gland. And while they are being displaced towards the center, the fat droplets keep on increasing in size as more fat accumulates. When these cells rupture at around the center of the gland, they are but fat-droplets lined by a cell membrane. This resultant mixture of fat and cellular debris after the rupture is sebum. Normally, sebum is excreted to the skin surface via the sebaceous duct and the hair follicle. When the production of sebum is excessive, the skin will appear greasy. However, if the outflow of sebum is somehow obstructed by a narrowing or blockage of the ductal lumen as a result of hyperkeratinization of the ductal epithelium, a comedo, which is the primary lesion in acne vulgaris, is formed.

The causes of hyperkeratinization of the ductal epithelium and sebum production are at present not known. However, there is good evidence to show that hyperkeratinization, similar to sebum production, starts with accumulation of fat droplets in the horny layer of the ductal epithelium. This may well imply that these two processes go hand in hand.

Though the etiology of acne vulgaris is not know because the basic changes in hyperkeratinization and sebum production are not understood, it is generally believed that genetic, bacterial, climatic and psychological factors are involved. But by far the most important single factor connected with the pathogenesis of acne appears to be hormonal, though the evidences are quite circumstantial. For example, the evidences indicate that the disease process is most frequently seen during puberty and adolescence; that the disease process often shows cyclic exacerbations premenstrually; that during pregnancy, the disease process often gets worse; that eunuchs, or females having ovariectomy done before puberty, do not have acnes; that ACTH administration in susceptible individuals of any age produces acne; and that ovarian tumors and adrenal tumors may be associated with acne.

While these are good reasons to suggest that acne vulgaris is closely related to hormones, they are not solid evidences to prove that these hormones produce acne. In fact, there are many pitfalls in these arguments. There is no explanation, for example, as to why certain individuals have acnes, while others with exactly the same hormonal make-up do not have acnes. Explanation is again lacking as to why the disease process occurs mainly during puberty and adolescence, with the incidence falling off sharply after the early twenties. There is no evidence whatsoever to suggest that the hormonal make-up of an individual will change after that period.

Some suggest that the male hormones, the androgens, are a potent stimulant of sebum production, and are responsible for the production of acne. But the very fact that the incidence of acne vulgaris is the same in both sexes refutes the argument. Even in the face of this, some still suggest that the androgens are indeed important in the pathogenesis of acne, but it is not the absolute amount of androgens that is significant, but rather, the sensitivity of the sebaceous glands towards the action of the hormones is more crucial. However, information is lacking as to the factors affecting such sensitivity and the suggestion is purely speculative.

The cyclic premenstrual exacerbation and the worsening of the disease process during pregnancy are not adequately explained. It is known that there is a steady decrease in sebum production during the first half of the menstrual cycle; in the luteal phase the excretion rate rises, only to fall again just premenstrually. The increase in sebum production in the luteal phase, with the clinical manifestation of the "premenstrual flare" and the worsening of the disease process during pregnancy, coincide with a period of a huge increase in progesterone secretion, but there is apparently no explanation to correlate this increase in progesterone level and acne production.

Even though it has been observed that eunuchs and females having ovariectomy done before puberty do not have acne, no study has been conducted to show that administration of sex hormones in these subjects will produce acne.

The reason why only susceptible subjects develop acne after ACTH administration is again not adequately explained, it is not understood why certain subjects are not susceptible. And in those who do develop acne, it is not clear whether the acne is due to a direct action of ACTH on the sebaceous glands, or whether it is due to an increase in level of adrenocorticoids or an increase in androgens of adrenocortical origin subsequent to the administration of ACTH.

All these only serve to show that the argument that hormones are responsible for the etiology of acne is unjustifiable and weak. The situation is indeed very perplexing and the evidences conflicting. However, if the theory of hormones is scrutinized more carefully, it is interesting to note that all the hormones involved are derived from cholesterol, (with the exception of ACTH; but ACTH stimulates the production of adrenocorticoid steroids, so that the end result is still a production of hormones derived from cholesterol) whose primary building blocks are the acetates in the form of acetyl-Co A. And Coenzyme A (Co A) is well known for its importance and the strategic position it occupies in fatty acid metabolism. And if the etiology of acne vulgaris is viewed from this angle, taking into account some of the observations associated with the disease process, it may be possible to form a novelty idea as to its pathogenesis, a novelty idea to explain the apparently very baffling situation.

There is a good reason for acne to develop at puberty. At puberty, there is a huge increase in production of the sex hormones to cater for the development of the primary and secondary sex organs. The demand for acetates, the biological active form of which is acetyl-Co A, is much increased because the acetates are the building blocks of cholesterol, the precursor of all the sex hormones. This is tantamount to an increase in demand for Coenzyme A, which in turn is equivalent to an increase in demand for pantothenic acid. A certain amount of pantothenic acid in the body is being channeled off for this purpose. As suggested in U.S. Pat. No. 5,039,698 relating to weight control, the use of pantothenic acid in the synthesis of the sex hormones seems to override the use of pantothenic acid in the metabolism of fat. Therefore, unless there is an abundant supply of pantothenic acid in the body, the portion that is rationed towards fat metabolism will be curtailed drastically. Consequently, there is a relative deficiency in the metabolism of fat that is proportional to the relative deficiency of pantothenic acid, and fat begins to accumulate in the body. Here, nature chooses to deposit these unmetabolized fat in the sebaceous glands in the form of fat droplets. If the supply of pantothenic acid is grossly deficient, its role in the metabolism of fat will be cut back drastically, and a lot of unmetabolized fat will be deposited in the sebaceous gland with the eventual increase in sebum production and the formation of acne. This explains why the sex incidence of the disease process is about equal.

There is little research conducted to study on the absolute amount of sex hormones that are required for the development of the primary and secondary sexual characteristics in the male or in the female during puberty and adolescence. But it seems that a fair amount will be required. The fact that eunuchs and females with a prepuberty ovariectomy do not have acnes suggests that in such instances, no sex hormones are secreted, with a consequence that a lot of pantothenic acid in the form of Coenzyme A will be spared to perform the less important function of fat metabolism, and very efficiently.

When the primary and secondary sexual characteristics are fully developed, in most instances in the mid to late teens, sex hormones and hence pantothenic acid requirements are less in demand. More pantothenic acid can be directed to discharge the function of fat metabolism, and the deficiency in fat metabolism becomes less and less significant. This is the reason why the incidence of the disease process drops rapidly after the late teens and the early twenties.

The same argument holds for the "premenstrual flare" during the latter part of the menstrual cycle. During that period, some pantothenic acid is diverted to perform the duty of progesterone synthesis, (the absolute amount of progesterones and estrogens secreted during this period is much more than the amount of estrogens and progesterones secreted in the follicular phase) resulting in an aggravation of the disease process.

The same explanation is true of pregnancy, ACTH administration, ovarian and adrenal tumors that are hormone-secreting. In certain such instances, the disease process can be really bad, almost uncontrolled. This is in line with the known fact that in some of these conditions, the amount of hormones produced can be very high, leading to an enormous shortening of supply of pantothenic acid towards fat metabolism.

It now seems clear that the basic pathology in the production of acne vulgaris is a shortening of supply of pantothenic acid. The role of the sex hormones in the pathogenesis is no longer perplexing. Its effect is mainly an indirect one. It is through a process of competitive inhibition of fat metabolism by vying with that process for the limited supply of pantothenic acid in the form of Coenzyme A. This explains why the effect of androgens and estrogens relating to acne vulgaris varies so much in different individuals, from the completely normal to the most severe form of acne, though the hormonal make-up in these people is probably similar. This is in accordance with the works of most investigators who found that boys with acne do not have higher testosterone levels than boys without acne. It is the availability of extra pantothenic acid in the body to discharge the duty of fat metabolism that is important. The question of sensitivity of the glands towards androgens, not to mention the factors affecting it, now seems irrelevant. The actions of contraceptive pills in the treatment of acne vulgaris is now obvious. It acts through the suppressant effect on ovulation, hence holding down the secretion of progesterone and sparing Coenzyme A for the metabolism of fat, and thus finally achieves a beneficial effect on the disease process. This also helps to explain the fact that progesterone has no effect on the treatment of acne, because administration of progesterone does not suppress the intrinsic secretion of the hormone, and lends no relief to the strained supply of Coenzyme A.

With all the evidences cited above, it is apparent that a deficiency in pantothenic acid must play a most important role in the pathogenesis of acne vulgaris. It has been explained above that an increase in synthesis of hormones that are derivatives of cholesterol and an increase in fat intake will proportionately deplete the body of pantothenic acid. But considering the strategic position pantothenic acid occupies in the metabolism of carbohydrate, fat and protein, and the myriad functions it has in the body, many of which are as yet poorly understood, chances are there must be a lot more of other conditions that are of higher priority than fat metabolism, that will consume considerable amount of pantothenic acid. And these conditions will, understandably, make the acne process worse. Perhaps psychological stress, so well known to make acne worse, falls into this category. So may be climatic factor and a lack of sleep, both of which may be considered as some form of stress. Acneigenic drugs and chemicals may also deplete a lot of pantothenic acid through some complicated detoxifying process. All these factors will make the disease process worse.

It has been mentioned earlier that the pathogenesis of acne vulgaris involves an increase in sebum secretion and an abnormal keratinization of the follicular epithelium, and that these two processes often go hand in hand. Indeed, there is good reason to believe that hyperkeratinization, like increased sebum secretion, is related to a deficiency in pantothenic acid leading to a deficiency in the mechanism of fat metabolism. One reason is that the very first sign of hyperkeratinization is an accumulation of fat droplets in the horny layer of the follicular epithelium, very similar to the accumulation of fat droplets in the sebaceous gland cells. The other reason is that structural lipids form an integral part of the cell membrane. Since it has been shown that increase in sebum secretion relates to a deficiency in the enzymic system of fat metabolism through a deficiency in pantothenic acid, it is not unreasonable to suspect that this deficiency in enzymic system of fat metabolism may alter the structural lipid of the cell membrane, ultimately leading to hyperkeratinization.

Another supporting evidence for this suggestion comes from the observation of an increase in pore size of the hair follicles, which is one of the very first signs of acne vulgaris. This is probably a physiological response to both an increase in sebum production and hyperkeratinization of the follicular ductal epithelium which will grossly narrow the lumen of the duct. Nature will try to offset the narrowing by a hypertrophy of the duct as a whole, resulting in a greatly enlarged pore size of the hair follicle. Administration of pantothenic acid has a striking effect on reducing the pore size of the hair follicle to its original minute size very early on, within just a few days of treatment. This suggests that pantothenic acid has its effect not only on sebum secretion, but that it probably has a direct effect on reversing the hyperkeratinization process, hence the already narrowed lumen is now wider. Consequently, the hypertrophic process is no longer necessary, and so is subsequently reversed. This is in contrast to what is seen when sebum of an acne lesion is being squeezed out of the follicle. There, despite an absence of sebum in the gland, the pore size of the hair follicle is unchanged. It remains large because the root of the trouble is not tackled.

If acne vulgaris bears such a close relationship to fat metabolism, it is only natural to investigate whether other vitamins, aside from pantothenic acid, playing their roles as coenzymes in the metabolic processes of fat metabolism, will affect the pathological process. Fat metabolism, like other metabolic processes in the body, is extremely complicated and involves many sets of interrelated enzyme systems, and in many instances, merges with carbohydrate and protein metabolism. It is, therefore, difficult to pinpoint exactly the enzyme systems, together with their coenzymes, that are directly involved in fat metabolism. However, it is generally believed that the vitamins nicotinic acid and biotin, playing their roles as coenzymes in various metabolic processes, are heavily involved in fat metabolism. And it has been shown in the present invention that administration of these two vitamins together with pantothenic acid will have a synergistic effect on the disease process.

BRIEF SUMMARY OF THE INVENTION

The present invention relates to the use of pantothenic acid, supplemented with nicotinic acid and biotin, in a dosage many, many times larger than the recommended daily allowance in treating acne vulgaris. This composition is believed to correct a deficiency in fat metabolism. This deficiency in fat metabolism is thought to be the basic pathology of the condition. In addition to correcting the deficiency in fat metabolism, these vitamins also are believed to exert a positive effect on the hyperkeratinization process, the cell membrane and the cell as a whole. In addition, it is believed that through the participation of pantothenic acid on the synthesis of the estrogens, the skin texture is improved by becoming more smooth and soft.

The method comprises the administration of pantothenic acid, supplemented with nicotinic acid and biotin, either orally, intramuscularly, intravenously, or rectally through a suppository, or the topical application of these agents onto the skin through a suitable carrier. Through the method the basic pathology of deficiency in fat metabolism is believed corrected and the cell and its membrane are altered in such a manner that the skin regains its smoothness, firmness, turgor and elasticity, culminating in achieving a retardation in the aging process of the skin in many cases.

Pantothenic acid is the principal agent of this treatment protocol, supplemented with nicotinic acid and biotin. A good initial dosage consists of approximately 2 to 10 gm of pantothenic acid, approximately 0.3 to 3 gm of nicotinic acid, and approximately 5 to 50 mg of biotin a day in 1 to 5 divided doses.

The composition is most conveniently administered orally in capsule form. A convenient dosage is 400 mg of pantothenic acid per capsule in pure powder form. Subjects given approximately 10 grams a day will mean taking 6 capsules (2.4 grams) at 4-hourly intervals 4 times a day. Nicotinic acid is also prepared in capsule form. A convenient dosage is 250 mg per capsule in pure powder form. To administer 1 gram, one capsule is taken four times a day. Biotin can also be prepared in capsule form in the dosage of 15 mg per capsule. A convenient interval for taking the medication is 4 times a day for both pantothenic acid and nicotinic acid and once a day for biotin. If the biotin is incorporated into either the pantothenic acid capsules or the nicotinic acid capsules, which means that the biotin is taken 4 times a day at 4-hourly intervals at the dosage level of 4 mg each time, it may even be better. The pantothenic acid, nicotinic acid and biotin may be incorporated together in a single capsule. Since both pantothenic acid and nicotinic acid are highly soluble, another convenient way of administration is to dissolve the daily dosage of 10 grams of pantothenic acid and 1 gram of nicotinic acid in 40 cc of a thin syrup in a suitable buffered system. Biotin, though quite insoluble, can be mixed into the same solution at the small dosage given as a thin suspension. The liquid can be taken in 4 divided doses at 4-hourly intervals.

The pantothenic acid, nicotinic acid and biotin composition can be admixed with a suitable base or carrier such as macrogols to form suppositories which may be administered rectally, the macrogols appear to be a suitable base for the suppository. An appropriate suppository may have the following composition: Macrogol 6000 (30% by weight), Macrogol 1540 (20% by weight), pantothenic acid (45% by weight), and nicotinic acid (5% by weight) with 1.5 mg of biotin added to each suppository. This will mean that a 2-gram suppository will contain 900 mg of pantothenic acid, 100 mg of nicotinic acid and 1.5 mg of biotin. The frequency of administration is again best at 4-hourly intervals.

Pantothenic acid and nicotinic acid are readily soluble in water and therefore can be effectively administered as an aqueous or saline solution via intramuscular or intravenous injection. Typically, such solution would contain about 10 mg of benzyl alcohol for indolence. The biotin being relatively insoluble in water may be administered orally in conjunction with the intramuscular or intravenous injection to provide the effective amount of each vitamin.

These agents can also be applied topically to the skin in any suitable, nontoxic, dermatologically acceptable vehicle containing approximately 0.5 to 25% by weight of pantothenic acid, 0.5 to 10% by weight of nicotinic acid, and 0.02 to 0.5% by weight of biotin. Preferably, the pantothenic acid, nicotinic acid, and biotin are present in the dermatologically acceptable carrier at a ratio of approximately 10:2.5:0.1, respectively. The number of applications can be about 1 to 6 and, preferably, 4 to 6 times a day. In fact, the more frequent the application, the better the result. A typical example of a dermatologically acceptable vehicle is a cream (aqueous based) made up of about 30% emulsifying ointment, 0.1% chlorocresol, and 69.9% purified water.

DEFINITIONS

The term "pantothenic acid" as used herein is intended to include pantothenic acid or a derivative thereof which generates pantothenic acid in the body.

The term "nicotinic acid" as used herein is intended to include nicotinic acid or a derivative thereof which generates nicotinamide adenine dinucleotide (NAD) or nicotinamide adenine dinucleotide phosphate (NADP) in the body.

DETAILED DESCRIPTION OF THE PREFERRED EMBODIMENTS

The purpose of the present invention is to effect a biochemical treatment or cure of the condition acne vulgaris. The present invention is based on the proposition that the fundamental pathology of acne vulgaris is a deficiency in fat metabolism. This deficiency in fat metabolism is caused by a shortening of supply of vitamins that serve as coenzymes in such metabolic processes. The most important vitamin relating to these metabolic processes is pantothenic acid. Nicotinic acid and biotin also contribute significantly to these processes. By replenishing the body with sufficient amount of these vitamins, through systemic administration or topical application to the affected areas, or by a combination of these two venues, the ultimate goal of prevention and cure of the disease process is achieved. And through the effect of these vitamins on the structure of the cell and cell membrane, and in particular, through the effect of pantothenic acid on the synthesis of estrogens, the skin becomes more firm, more smooth, more elastic and more turgid. Ultimately, the skin looks younger and the effect of retardation of aging of the skin is achieved.

Since the treatment of the condition with a sufficient amount of the vitamins is directed at the root of the trouble, the treatment process is expected to be very efficient and very effective.

Once treatment is initiated, if the dosage is large enough, the response is almost immediate, usually within two or three days of initiating treatment. The first noticeable change is that there is a decrease in sebum secretion on the acne bearing area, notably the face. This is of course due to a decrease in the activity of the sebaceous glands. Normally, following an increase in sebum secretion, a full-blown lesion goes through the stages of an eruption of comedone, then a papule is formed, followed by the formation of pustule, cyst, nodule and finally scar. Within days of onset of treatment, which probably represents the building up of the vitamins to an optimum level, and following the reduction of sebum production, the development of the comedones and papules is arrested. For pustules and cysts, because the element of infection has already set in, reversing the disease process will be difficult. They have to be dealt with in the conventional manner by expressing and draining the contents. Administration of a short course of antibiotics in such instances is well indicated. When these pustules and cysts are all healed, antibiotics should no longer be required, as any such new lesions are not expected to develop from the existing papules. Instead, the papules and comedones will start to subside, making the skin much more smooth. This is especially noticeable when the comedones are deeply seated. The normal course of events is for these comedones and papules to grow, to ripe, before they can reach the skin surface and be expressed and drained. With the fat metabolism corrected, these lesions will not grow, instead, they will shrink in the course of a few days. So that, in a matter of weeks, all the lesions will resolve.

Unless the lesion has gone so far as to reach the stage of infection, the lesion is still in a reversible state, provided that enough of the vitamins are administered. Sometimes, when the individual is badly affected by the disease process, even with a large daily dosage of the vitamins, the disease process will take some time to respond. This is because the body has to be saturated with the vitamins before they can exert their effect on the acne lesions. This seems to suggest that, of the many functions these vitamins have to perform in the body, fat metabolism relating to acne vulgaris occupies a very low position in the priority list. It is interesting to note that individuals on weight control with pantothenic acid will frequently develop acne vulgaris when the calorie intake is really low, even if these individuals normally have no inclination to develop acne. This strongly suggests that in fat metabolism, the relief of starvation overrides the relief of acne vulgaris. During this initial stage of treatment, when the body is still in the process of saturating itself with the vitamins, new lesions will continue to form. However, once the body is saturated with these vitamins, new lesions will stop coming up, while at the same time, the already formed lesions will begin to subside. The rapidity of response is related to the dosage administered, up to a certain limit, beyond which the response levels off.

For the more severe form of acne lesions, once infection sets in there is no way to deal with the lesion except to drain it, either by expressing it manually, or to wait for it to burst through the skin naturally. Once pus is drained, with a sufficient amount of vitamins in the body, the subsequent response will be the same as a comedo in its formation. Under normal circumstances, the response is prompt. With the pustules and cysts drained and treated, the whole disease process is under control. Continual administration of the vitamins will lead to rapid subsidence of the existing lesions, and new lesions will not be formed. A concomitant administration of antibiotics in such instances will be very helpful. This is because new papules will not be formed, not to say its further progression into pustules and cysts. However, because of the severity of the disease, implying that the vitamins are in extreme short supply, significant improvement will take a longer time, maybe 4 to 5 weeks. Aside from the already gross deficiency of the vitamins in the body, which by itself will take a longer time to replenish, another possible reason may be related to an impairment of absorption of these vitamins from the bowel, otherwise the disease process would not be so bad to begin with. This will make a satisfactory blood level more difficult to achieve so that a longer period of time will be required for the clinical response to be observed. Here again, once good clinical response is observed, the eventual progress will be sure and steady. In most instances, excellent response is achieved within 3 months of treatment. It is interesting to note that in these patients with severe acne lesions, many already have previous scars left on their face, some of the deeper scars with an uneven base actually become less conspicuous. For more shallow scars, the change is less obvious.

One of the earliest and most striking responses seen with this form of treatment is that the pore size of the hair follicle is reduced. An enlarged pore size of the hair follicle is a constant feature of acne vulgaris, and contributes much to the rough look of the facial skin of acne patients. As explained, this is in part a physiological response to increased sebum secretion and in part relates to the hyperkeratinization process of the follicular ducts. In order to discharge the sebum produced in excessive quantity, the natural thing the gland will do is to increase the size of the pore and the ductal system in an attempt to relieve the obstruction that is likely to ensue. This is the hypertrophy process of the ductal system. However, at this stage of the disease process, there is the hyperkeratinization of the ductal epithelium going on, and this process will narrow the ductal diameter, and will cancel out the original purpose of the hypertrophy process. So, in order to achieve the original intention of making the conduit bigger, the hypertrophic process of the ductal system is further enhanced. This is the reason why the pore size is so greatly enlarged. With the basic deficiency problem corrected by administration of these vitamins relating to fat metabolism, sebum secretion is reduced, and physiologically, a wide-bored hair follicle is no longer required. And since the hyperkeratinization process is also reversed by these vitamins, thus making the ductal system more patent, the whole ductal system can be further reduced so that the size of the hair follicle is greatly and noticeably reduced. This feature of reducing the pore size of the hair follicle alone will make the facial skin a lot finer and younger, very similar to the skin of individuals before puberty.

There are, however, two other factors that are thought to play a part in making the skin look younger. There is the direct action of the vitamins on fat metabolism relating to the cell as a whole, and to the cell membrane.

The lipids in the body cells are of 2 main types: structural lipids, which form a very important part of the cell membranes and also other parts of the cell; and neutral fat, stored in the adipose cells of the fat depots.

The structural lipids consist of the following:

(1) Phospholipids or phosphoglycerides including lecithin or choline phosphoglyceride and cephalin or ethanolamine phosphoglyceride.

(2) Cholesterides which are cholesterol esters of fatty acids.

(3) Certain specialized lipids like the sphingomyelins and cerebrosides of the central nervous system.

The biosynthesis of these structural lipids requires the participations of many different enzyme systems. Many of these have pantothenic acid, nicotinic acid, and biotin as their coenzymes. This is particularly true of pantothenic acid. It is easy to visualize that the integrity of the cell membrane and the cell as a whole depends very much on these vitamins. With the administration of these vitamins in the course of treatment of acne vulgaris, it is observed that there is definite improvement of the smoothness, firmness, turgidity and elasticity of the skin, particularly the facial skin, making the individual look younger. It is interesting to note that the skin of the face benefits more from the treatment than the other parts of the body skin. This probably relates to the fact that the skin of the face, being exposed to the sun and the weather, and is commonly referred to as the weather-beaten face, is being depleted of the vitamins locally during the wear and tear process, and is being insufficiently replenished because there is an overall deficiency of the vitamins. Replacement of these vitamins will eventually return the texture of the skin to its former state.

The other factor that may play a part in making the skin look younger probably acts through the effect of the estrogen group of hormones. It is known that the estrogen group of hormones causes the skin to develop a texture that is soft and smooth that is characteristic of the female skin, and will generally make the skin look younger. When there is a very strained supply of pantothenic acid, even though there is a preference in synthesis of the hormones, the optimal amount that is required may not be synthesized. With a liberal replacement of pantothenic acid, the optimal amount of estrogens will be synthesized, and the skin will respond by developing the typical feminine texture that will make the skin feel and look younger. Although estrogen is known to make the skin younger, it is seldom administered systemically to achieve this aim, even for the females. The reason is due to the fact that estrogen administration, usually for replacement therapy, aside from having some very unpleasant side effects, is known to have a certain risk of developing cancer. The cause of carcinogenesis is not known. Here is a situation where a naturally occurring hormone, once it is being used as a replacement agent, will have the undesirable effect of causing cancer. The probable answer lies in the dosage. It has to be remembered that there is a biochemical variability in the requirements of hormones between individuals. And the exact dosage is different for each individual. The optimal amount that is required is finely tuned by the auto-regulatory mechanism of the body. Any excess in amount will have some very undesirable effects. Furthermore, the estrogens in fact represent a group of different hormones whose precise functions in the body, the delicate balance of their ratio in terms of absolute amount have not been defined. Normally, the body depends on the auto-regulatory system to sort out the details, and it is probably a delicate balance of these hormones, in terms of composition and dosage, that ensure the body to function smoothly, without producing any objectionable effects, not to say the development of cancer. Replacement therapy of the estrogens, whatever the combinations and the dosage, will somewhat upset this delicate balance, with a consequence that a small proportion of individuals will develop cancer and other side effects. Administration of pantothenic acid, however, can achieve the best possible effect by leaving everything to the auto-regulatory system, whereby the body, be it a male or a female, will have the optimal level of the estrogens in the blood to make the skin look young, and yet can sidestep all the untoward effect of estrogen.

Trials of the three vitamins separately and in combinations have been conducted. Various dosages have also been tried. It has been found that, when administered separately, pantothenic acid is always by far the most effective agent. Nicotinic acid is also effective, but is definitely less potent than pantothenic acid. It has an added disadvantage in that, when given in high dosage in the region of 5 gm or more a day, there is a possibility that the patient may suffer from its side effects, notably hepatotoxicity with liver enzyme elevation. Biotin is one of the most active biological substances known. As a single agent, its effectiveness is probably less than even nicotinic acid. However, it has the advantage that when given in a dosage as high as 20 mg a day, there is no side effect observed. And in terms of absolute quantity, this is a much smaller dosage than is required of either pantothenic acid or nicotinic acid.

Using pantothenic acid as the principal agent, combinations of these three vitamins in various strengths were tested. It is found that these three vitamins tend to potentiate each other's effect. That is to say, they tend to have a synergistic effect. While there are clear biochemical variabilities between different individuals, and depending on their own specific deficiencies in the vitamins, and unless the disease process is so mild that as little as 2 gm may suffice, it is found that a good initial dosage for treatment would consist of a daily dosage of approximately 2 to 10 gm of pantothenic acid, supplemented by approximately 0.3 to 3 gm of nicotinic acid, and approximately 0.5 to 50.0 mg of biotin. The vitamins can be administered individually or in combination. Preferably, the vitamins are combined and administered at about 4-hour intervals so that up to about 5 doses per day are administered. In mild to moderate cases, the response is always very prompt. In just a few days, a good response is normally observed. In severe cases, it may take a few more days for the body to saturate itself with these vitamins before any effect is observed. In any case, a good clinical response is always observed within the first two weeks of treatment irrespective of the initial condition. And, once clinical response is observed, the subsequent response is always steady and satisfactory.

Because of the nontoxic nature of these vitamins even at high dosage, the treatment regimen involving dosages that are many times above the recommended daily allowance for each of the three vitamins can be continued week after week, without reducing the dosage and without any worry that there may be any side effects developing. The treatment is continued until all the lesions have subsided. Depending on the severity of the condition, this treatment period varies from patient to patient. Unless the condition is very severe, the length of treatment normally is less than 12 weeks. And in many instances, it takes a much shorter time. Normally, by the time all the acne lesion subsides, the body will be so saturated with the vitamins that cessation of treatment for a limited period of time will not lead to the recurrence of the disease process. However, with these patients, there is probably a problem with their absorption of the vitamins, or due to some biochemical variation, there is a higher requirement of these vitamins, the disease process frequently recurs after a period of time, though the severity is much less most of the time. For this reason, it is always advisable to put these patients on a maintenance regimen. Because of the wide range of biochemical variation between individuals, the maintenance dosage varies from individual to individual. On the average, even for those that are severely affected, a daily maintenance dosage consisting of about 2 gm of pantothenic acid, about 300 mg of nicotinic acid and about 5 mg of biotin is normally sufficient. For those that are only mildly affected, a lower maintenance dosage is possible. For those who still have occasional acne eruptions, the simple thing to do is to increase the pantothenic acid dose.

The effect of the vitamins on the skin texture begins very soon after the commencement of the treatment regime. In about 2 to 3 weeks, the skin, especially the facial skin and the skin that is normally exposed, shows signs of increased smoothness, and is more turgid and elastic. This effect of the vitamins on the structure of the cells and cell membranes, and indirectly through the action of estrogens has been explained earlier.

The treatment regimen is aided by the topical application of creams made up of pantothenic acid in concentration of approximately 0.5 to 25% by weight, nicotinic acid in concentration of approximately 0.5 to 10% by weight, and biotin in concentration of approximately 0.02 to 0.5% by weight.

Preferably, the pantothenic acid, nicotinic acid and biotin are present in the dermatologically acceptable carrier at a ratio of approximately 10:2.5:0.5, respectively. Treatment of acne vulgaris with topical application alone is effective in certain mild cases. In more severe cases, its role is more of a supportive nature in supplementing systemic treatment. Even with maintenance therapy, topical application about 1 to 6 times a day is more of an adjuvant nature to that of systemic therapy.

Aside from the effectiveness obtained from administration of these vitamins, either systemically or topically, or a combination of sytemic and topical application, another major benefit from this treatment protocol is that there are no side effects experienced and that there are no contraindications to its application. This is because these agents are vitamins, they are natural foods required by the body, and hence have no unwanted side effects, even at the high dosage level recommended.

A brief account of the three vitamins is perhaps warranted here.

1. Pantothenic Acid

Chemistry

Pantothenic acid, (+)-(R)-3-(2,4-Dihydroxy-3,3-dimethylbutyramido)propionic acid, is an optically active organic acid and biological activity is characteristic only of the disomer. The vitamin functions in the body following its incorporation into Coenzyme A.

Pharmacological Actions

Pantothenic acid has no outstanding pharmacological actions when it is administered to experimental animals or normal man. The vitamin is essentially nontoxic; as much as 10 gm can be given daily to man without producing symptoms. See, Dumm, M. E. and Ralli, E. P., *Metabolism* 2, 153 (1953). In accordance with *MARTINDALE, The Extra Pharmacopoeia* (1989), the adverse effects of pantothenic acid consist of just one sentence: "Pantothenic acid is reported to be generally nontoxic."

Physiological Functions

Coenzyme A, the physiological active form of pantothenic acid, serves as a cofactor for a variety of enzyme-catalyzed reactions involving transfer of acetyl (two-carbon) groups; the precursor fragments of various lengths are bound to the sulfhydryl group of Coenzyme A. Such reactions are important in the oxidative metabolish of carbohydrates, gluconeogenesis, synthesis and degradation of fatty acids, and the synthesis of sterols, steroid hormones, and porphyrins. See, Wright, L. D., "Pantothenic Acid", *Present Knowledge in Nutrition,* The Nutrition Foundation, Washington, D.C., pp. 226–231 (1976).

Human Requirements

According to *MARTINDALE, The Extra Pharmacopoeia,* 29th Edition (1989), "Pantothenic acid is widely distributed in foods. Meat, legumes, and whole grain cereals are particularly rich sources; other good sources include eggs, milk, vegetables, and fruits. Recommended daily intakes of pantothenic acid have not been set in the U.K. or in the U.S., but human requirements are adequately met by a daily intake of about 4 to 10 mg." According to Goodman and Gilman's *The Pharmacological Basis of Therapeutics,* "Pantothenic acid is a required nutrient, but the magnitude of need is not precisely known. Accordingly, the Committee on Dietary Allowances provides provisional amounts in the form of ranges of intakes (in different age groups). For adults, the provisional allowance is 4 to 7 mg per day. Intakes for other groups are proportional to calorie consumption. (Thus, infants will require 2–3 mg per day, children and adolescents 3–7 mg per day.) In view of the wide-spread distribution of pantothenic acid in foods, dietary deficiency is very unlikely."

2. Nicotinic Acid

Chemistry

Nicotinic acid is chemically pyridine- 3-carboxylic acid. It is a white, odorless or almost odorless, crystal or crystalline powder. It is also known as niacin, a term introduced to avoid confusion between the vitamin and the alkaloid nicotine. Nicotinic acid functions in the body after conversion to either nicotinamide adenine dinucleotide (NAD) or nicotinamide adenine dinucleotide phosphate (NADP). It is to be noted that nicotinic acid occurs in these two nucleotides in the form of its amide, nicotinamide, so that, for practical purposes, administration of nicotinic acid or nicotinamide are one and the same thing.

Adverse Effects

Nicotinic acid produces frequent adverse effects, but they are usually not serious, tend to decrease with time, and can be managed easily. The exact dosage that will give rise to adverse effects probably varies from individual to individual, and is difficult to determine. However, it is mentioned in *MARTINDALE, The Extra Pharmacopoeia* (1989), that massive doses of nicotinic acid, usually 3 to 6 gm daily as a hypolipidaemic agent, has been administered and studied in several clinical trials, with some side effects being observed. And in the present study, adverse effects have not been observed with a maximum daily dosage of 1.0 gm. In fact, this complete absence of side effects of nicotinic acid at 1.0 gm a day is unique, and may be related to the simultaneous administration of pantothenic acid. It is not an uncommon experience to note that when the B complex vitamins are prescribed to patients in dosages ranging from a few times to a dozen times higher than the Recommended Daily Allowance, acne vulgaris lesions begin to erupt a few days after the initiation of treatment. The following is a possible explanation. During the administration of the B complex vitamins, the biochemical reactions requiring the participation of these vitamins are potentiated due to the increase in concentration of these vitamins. These chains of biochemical reactions may also require the participation of pantothenic acid, so that pantothenic acid reserved for fat metabolism actually decreases despite the fact that it is also included in the B complex. This is because the amount of pantothenic acid included in the B complex is just not enough. Other acneigenic drugs probably act through the same mechanism of depleting that portion of pantothenic acid that is reserved for fat metabolism. To reason along this line, it can be said that the "side effects" of acne due to the B complex can be relieved by pantothenic acid. Similarly, the various side effects of nicotinic acid is being relieved by the simultaneous administration of pantothenic acid.

Human Requirements

The recommended allowance of the Dietary Allowances Committee of the National Research Council, expressed in nicotinic acid equivalents, is 6.6 mg/1000 kcal. For people who consume few calories, daily intake should not fall below 13 mg.

3. Biotin

Chemistry

Biotin is also known as Coenzyme R or Vitamin H. Chemically, it is cis-5-(Hexahydro-2-oxo-1H-thienol- 3,4-d-imidazol-4-yl) valeric acid. It is a practically white, crystalline powder, and is only very slightly soluble in water and in alcohol.

Adverse Effects and Pharmacological Actions

Relatively large amounts of biotin have been administered to man with impunity. As a therapeutic agent, large doses, 5 to 10 mg daily, are administered to babies with infantile seborrhea with very good response and no adverse effects.

Human Requirements

The daily requirement of adults for biotin has been assigned a provisional value of 100 to 200 micrograms by the Committee on Dietary Allowances.

Experimental Examples

About 100 patients with acne vulgaris in varying degrees of severity, aged between 10 and 35 (the majority being in the range of 13 to 25) were given a combination of approximately 10 gm of pantothenic acid, 1.0 gm of nicotinic acid and 15 mg of biotin daily in divided doses four times a day. A cream containing 20% of pantothenic acid, 5% of nicotinic acid, and 0.2% of biotin by weight was also applied to the affected area 4 times a day. Within a few days, the secretion of sebum was markedly reduced, resulting in a much less greasy appearance. Unless the disease process was very severe, the acne lesions also responded by regressing in size within the first few days of initiating treatment. New eruption became noticeably fewer. Pore size of the hair follicles became smaller. The improvement was further enhanced if the patient adhered to a diet containing little or reduced oily or creamy foods. A premenstrual flare was normally still present initially, though the degree was definitely a lot less. This probably relates to the fact that the body initially is quite depleted of the vitamins, particularly pantothenic acid. However, with a few more weeks of treatment, by the time the next period occurred, the premenstrual flare was minimal.

As a matter of academic interest, 20 patients were put on the systemic treatment only without the concomitant local application of the creams, and 20 patients were treated with local application of the cream only. It was found that those who were treated with systemic therapy only, the result was still extremely good, except that the response was just a bit delayed because with local application, the concentration of the vitamins is achieved sooner. However, with local application of the cream alone, though a definite clinical response was still achieved, it never completely eradicated the disease process unless the nature of the disease process was very mild.

All this time, about 2 to 3 weeks after the treatment began, the existing acne lesions continued to subside. New lesions only came up very occasionally. Along with the decrease in size of the pore of the hair follicles, the skin became more smooth, firmer, more elastic and more turgid, making the appearance much younger. The patient was more agile together with an improvement of the general well-being. In fact, this improvement in agility and general well-being was even more remarkable with these acne patients than the patients being put on a low calorie diet, further enhancing the belief that pantothenic acid is a most important vitamin in the body. With due consideration of its effect on the cell as a whole and on the cell membrane, its strategic position in the common metabolic pathway, and its ubiquitous occurrence in the cells (which is another implication of its importance), it will come as no surprise that pantothenic acid may eventually prove to be an anti-aging factor to the organism as a whole. That is to say, it not only improves the appearance and texture of the skin, but it has the potential of improving the longevity of the organism as a whole. However, to prove this point, a long-term study will be necessary.

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

What is claimed is:

1. A method for treatment of acne vulgaris which comprises administering to a patient suffering from acne vulgaris a combination of pharmaceutical agents consisting essentially of:

(1) approximately 2 to 10 grams pantothenic acid;

(2) approximately 0.3 to 3 grams nicotinic acid; and (3) approximately 5 to 50 milligrams biotin, said combination of pharmaceutical agents being administered to said patient systemically in divided doses about 1 to 5 times a day.

2. The method of claim 1 wherein said combination of pharmaceutical agents is administered as a mixture.

3. The method of claim 2 wherein said mixture is administered to said patient orally, or rectally.

4. The method of claim 3 wherein said mixture is administered to said patient orally in the form of capsules, tablets or a liquid.

5. The method of claim 4 wherein said mixture is administered to said patient in the form of capsules.

6. The method of claim 1 wherein said pantothenic acid and said nicotinic acid are administered to said patient intramuscularly or intravenously, and said biotin is administered orally.

7. The method of claim 1 wherein said combination of pharmaceutical agents is supplemented with an adjuvant pharmaceutical composition applied topically to the skin of said patient, said adjuvant composition consisting essentially of a dermatologically-acceptable, aqueous-based cream carrier containing approximately 0.5 to 25% by weight pantothenic acid, approximately 0.5 to 10% by weight nicotinic acid, and approximately 0.02 to 0.5% by weight biotin, the balance of said adjuvant composition being said dermatologically-acceptable, aqueous-based cream carrier.

8. The method of claim 7 wherein said pantothenic acid, said nicotinic acid, and said biotin in said adjuvant pharmaceutical composition are present in a weight ratio of about 10:2.5:0.1 said adjuvant pharmaceutical composition being applied to said skin of said individual 5 or 6 times a day.

9. The method of claim 1 wherein said combination of pharmaceutical agents is administered to said patient orally, or rectally.

10. The method of claim 9 wherein said combination of pharmaceutical agents is administered orally in the form of capsules, tablets or a liquid.

11. The method of claim 10 wherein said combination of pharmaceutical agents is administered orally in the form of capsules.

12. A method for treatment of acne vulgaris which comprises applying to the affected areas of a patient suffering from acne vulgaris a topical composition consisting essentially of a dermatologically-acceptable aqueous based cream carrier containing approximately 0.5 to 25% by weight pantothenic acid, approximately 0.5 to 10% by weight nicotinic acid, and approximately 0.02 to 0.5% by weight biotin, the balance of said topical composition being said dermatologically-acceptable aqueous based cream carrier.

13. The method of claim 12 wherein said dermatologically-acceptable, aqueous based cream carrier contains said pantothenic acid, said nicotinic acid, and said biotin in a weight ratio of approximately 10:2.5:0.1, said composition being applied to said affected areas about 1 to 6 times a day.

14. A method for preventing the recurrence of acne vulgaris in a patient in which the clinical condition associated with acne vulgaris have been alleviated which comprises applying to the skin of said patient a topical composition consisting essentially of a dermatologically-acceptable, aqueous based carrier containing approximately 0.5 to 25% by weight pantothenic acid, approximately 0.5 to 10% by weight nicotinic acid, and approximately 0.02 to 0.5% by weight biotin, the balance of said topical composition being said dermatologically-acceptable, aqueous based cream carrier.

15. The method of claim 14 wherein said dermatologically-acceptable, aqueous-based cream carrier contains said pantothenic acid, said nicotinic acid, and said biotin in a weight ratio of approximately 10:2.5:0.1, said composition being applied to said patient about 1 to 6 times a day.

16. A method for preventing the recurrence of acne vulgaris in a patient in which the clinical conditions associated with acne vulgaris have been alleviated which comprises administering to said patient a combination of pharmaceutical agents consisting essentially of:

(1) up to approximately 2 grams pantothenic acid;

(2) up to approximately 0.3 grams nicotinic acid; and (3) up to approximately 5 milligrams biotin, said combination of pharmaceutical agents being administered to said patient systemically in divided doses about 1 to 5 times a day wherein said combination of pharmaceutical agents is supplemented with an adjuvant pharmaceutical composition applied topically to the skin of said patient, said adjuvant composition consisting essentially of a dermatologically-acceptable, aqueous-based cream carrier containing approximately 0.5 to 25% by weight pantothenic acid, and approximately 0.5 to 10% by weight nicotinic acid, and approximately 0.02 to 0.5% by weight biotin, the balance of said adjuvant composition being said dermatologically-acceptable, aqueous-based cream carrier.

17. The method of claim 16 wherein said combination of pharmaceutical agents is administered to said patient orally in the form of capsules, tablets or a liquid.

18. The method of claim 17 wherein said combination of pharmaceutical agents is administered to said patient orally in the form of capsules.

19. The method of claim 16 wherein said pantothenic acid, said nicotinic acid, and said biotin in said adjuvant pharmaceutical composition are present in a weight ratio of about 10:2.5:0.1, said adjuvant composition being applied topically to said skin of said patient about 1 to 6 times a day.

20. A pharmaceutical composition consisting essentially of:

(1) approximately 2 to 10 grams pantothenic acid;

(2) approximately 0.3 to 3 grams nicotinic acid; and (3) approximately 5 to 50 milligrams biotin.

21. A pharmaceutical composition which consists essentially of a dermatologically-acceptable, aqueous-based cream carrier containing approximately 0.5 to 25% by weight pantothenic acid, approximately 0.5 to 10% by weight nicotinic acid, and approximately 0.02 to 0.5% by weight biotin, the balance of said pharmaceutical composition being said dermatologically-acceptable, aqueous-based cream carrier.

22. The composition of claim 21 wherein said pantothenic acid, said nicotinic acid, and said biotin are present in said composition in a weight ratio of approximately 10:2.5:0.1.

* * * * *